(12) United States Patent
LaFace (10) Patent No.: US 6,649,158 B1
(45) Date of Patent: Nov. 18, 2003

(54) METHODS AND COMPOSITIONS TO INDUCE ANTITUMOR RESPONSE

(75) Inventor: Drake M. LaFace, San Diego, CA (US)

(73) Assignee: Canji, Inc., San Diego, CA (US)

( * ) Notice: Subject to any disclaimer, the term of this patent is extended or adjusted under 35 U.S.C. 154(b) by 0 days.

(21) Appl. No.: 09/416,813

(22) Filed: Oct. 13, 1999

Related U.S. Application Data (60) Provisional application No. 60/104,370, filed on Oct. 15, 1998.

(51) Int. Cl.$^7$ .................. A01N 63/00; C12N 21/06; C12N 19/52; C12N 15/00; C12N 5/00

(52) U.S. Cl. .................. 424/93.17; 435/69.1; 435/83; 435/320.1; 435/325

(58) Field of Search .................. 435/320.1, 69.1, 435/83, 325; 514/44; 424/93.17

(56) References Cited

U.S. PATENT DOCUMENTS

| | | | |
|---|---|---|---|
| 5,677,178 A | | 10/1997 | McCormick |
| 5,747,469 A | * | 5/1998 | Roth et al. .................. 514/44 |
| 5,830,880 A | * | 11/1998 | Sedlacek et al. ............ 514/44 |

FOREIGN PATENT DOCUMENTS

| | | | |
|---|---|---|---|
| WO | WO 95/11984 A2 | | 5/1995 |
| WO | WO 96/06940 | * | 3/1996 |
| WO | WO97/22438 | * | 7/1997 |
| WO | WO 98/15285 A1 | | 4/1998 |
| WO | WO 98/21228 A1 | | 5/1998 |
| WO | WO 98/21330 A1 | | 5/1998 |
| WO | WO 98/39464 A3 | | 9/1998 |
| WO | WO 99/47169 A1 | | 9/1999 |

OTHER PUBLICATIONS

Ogawa et al. Novel Combination Therapy for Human Colon Cancer with Adenovirus Mediated Wild–Type p. 53 Gene Transfer and DNA Damaging Chemotherapeutic Agent Sub. J. Cancer 73:367–370, 1997.*
Song et al. Sensitization of cis–Platimun by a Recombinant Adenovirus Vector Expressing Wild–Type p53 Gene in Human Ovarian Carcinomas. Oncology Res. 9: 603–609, 1997.*
Zhang et al. Gene Therapy Strategies for Cancer Exp. Opiu. Invest. Drugs. 4(6):487–514, 1995.*
Deonarian M., "Ligand–targeted receptor–mediated vectors for gene delivery."0 Exp. Opin. Ther. Patents, vol. 8 (1): 53–69, 1998.*
Miller et al., "Targeted vectors for gene therapy." FASEB, vol. 9:190–199, 1995.*
Eck et al., "Gene–based therapy." Goodman & Gilman's The Pharmacological Basis of Therapeutics– Ninth Edition, McGraw–Hill: 77–101, 1996.*
Parr et al., "Tumor–selective transgene expression in vivo mediated by an E2F–responsive adenoviral vector". Nature Medicine, vol. 3 (10): 1145–1149, Oct. 1997.*
Greaves et al., J. Exp. Med., vol. 186(6): 837–44, 1997.*
Crystal R., "Transfer of genes to humans: Early lessons and obstacles to success." Science, vol. 270: 404–410, 1995.*
Verma et al., "Gene therapy–promises, problems and prospects." Nature, vol. 389: 239–242, Sep. 1997.*
Braciak et al.; Overexpression of RANTES Using a Recombinant Adenovirus Vector Induces the Tissue–Directed Recruitment of Monocytes to the lung, 1996, The American Association of Immunologists: 5076–5084.*
Rossi et al.; Identification Through Bioinformatics of Two New Macrophage Proinflammatory Human Chemokines, 1997, J. Immunol 158(3): 1033–1036.*
Jain; Delivery of molecular and cellular medicine to solid tumors, 1998, Journal of Controlled Release 53: 49–67.*
Hobbs et al.; Regulation of transport pathways in tumor vessels: Role of tumor type and microenvironment, 1998, Proc. Natl. Acad. Sci., vol. 95: 4607–4612.*
Banchereau et al.; Dendritic cells and the control of immunity, 1998, Nature vol. 392: 245–252.*
Caux et al.; Dendritic cell biology and regulation of dendritic cell trafficking by chemokiness, 2000, Springer Semin Immunopathol 22: 345–369.*
Babiss et al.; Cellular Promotes Incorporated into the Adenovirus Genome, 1987, J. Mol. Biol. 193: 643–650.*
Shi et al.; Modulation of the Specificity and Activity of a Cellular Promoter in an Adenoviral Vector, 1997, Human Gene Therapy 8: 403–419.*
Curiel; Strategies to Adapt Adenoviral Vectors for Targeted Delivery: 158–171.*
Gomex–Navarro et al.; Gene Therapy for Cancer, 1999, European Journal of Cancer, vol. 35, No. 6:867–885.*
Li et al.; Loss of Adenoviral Receptor Expression in Human Bladder Cancer Cells: A Potential Impact on the Efficacy of Gene Therapy, 1999, Cancer Research 59: 325–330.*

(List continued on next page.)

Primary Examiner—Deborah Crouch
Assistant Examiner—Joseph Woitach
(74) Attorney, Agent, or Firm—Richard B. Murphy (57) ABSTRACT

The present invention provides compositions which are engineered to induce killing of tumor cells and concomitantly mobilize differentiate, activate and attract dendritic cells through the expression of cytokines and dendritic cell chemoattractants. The present invention invention is induces multiple stages of dendritic cell differentiation, activation and migration in vivo using gene therapy delivery systems. Moreover, this invention describes the rational design of utilizing viral vectors (preferred vector is rAd) for multiple administrations of targeted delivery to dendritic cells which can promote differentiation and activation of the transduced dendritic cells (thus augmenting in vivo stimulation of T cells, NK cells and B cells. The present invention provides a method to induce an antitumor immune response through the use of such compositions.

5 Claims, 2 Drawing Sheets

OTHER PUBLICATIONS

Hemmi et al.; ThePresence of Human Coxsackievirus and Adenovirus Receptor Is Associated with Efficient Adenovirus . . . Melanoma Cell Cultures, 1998, Human Gene Therapy 9: 2363–2373.*

Li et al.; Variability of Adenovirus Receptor Density Influences Gene Transfer Efficiency and Therapeutic Response in Head and Neck Cancer, 1999, Clinical Cancer Research vol. 5: 4175–4181.*

Hallenbeck et al.; Targetable Gene Delivery Vectors, 2000, Cancer Gene Therapy : 37–46.*

Song, et al., (1997), Dendritic Cells Genetically Modified with an Adenovirus Vector Encoding the cDNA for a Model Antigen Induce Protective and Therapeutic Antitumor Immunity, J. Exp. Med. vol. 186, No. 8, pp. 1247–1256.

Sherman, et al., (1998), Strategies for Tumor Elimination by Cytotoxic T Lymphocytes, Critical Reviews in Immunology vol. 18, pp. 47–54.

Dieu, et al., (1998), Selective Recruitment of Immature and Mature Dendritic Cells by Distinct Chemokines Expressed in Different Anatomic Sites, J. Exp. Med. vol. 188, No. 2, pp. 373–386.

Ishida, et al., (1999), Dendritic cells tranduced with wild–type p53 gene elicit potent anti–tumour immune responses, Clin. Exp. Immunosol vol. 117, pp. 244–251.

He, et al., (1996), Construction of adenoviral and retroviral vectors coexpressing the genes encoding the hepatitis B surface antigen and B7–1 protein, Gene vol. 75, pp. 121–125.

* cited by examiner

METHODS AND COMPOSITIONS TO INDUCE ANTITUMOR RESPONSE

This application claims the benefit of U.S. Provisional Application Serial No. 60/104,370 filed Oct. 15, 1998 pursuant to 35 U.S.C. 119.

BACKGROUND OF THE INVENTION

The immune system has evolved to process and recognize intracellular antigens via a class I MHC mediated antigen presentation pathway. Class I MHC restricted antigens are targeted by CD8 positive T cells largely consisting of cytotoxic T cells (CTL). An essential property of tumor antigen recognition by CD8 positive CTL cells is the requirement of the TCR to engage class I MHC/peptide complexes. Class I MHC restricted peptides are customarily derived from intracellular proteins. Thus, stimulation of immunity following in vivo administration of recombinant proteins preferentially stimulates antibody responses and only weak CTL responses.

Based on these fundamentals of CTL recognition, several methods have traditionally been utilized to stimulate CTL responses. Peptides with conanical sequences optimized for MHC class I binding can displace non-covalently bound peptide on cell surface MHC class I in a concentration dependent manner. Peptides have successfully been utilized to stimulate CTL responses in vivo but generally require the use of adjuvants such as IFA. Alternatively, genetic approaches such as viral vectors or naked DNA have been utilized to introduce gene sequences directly into cells to expression intracellularly to deliver antigen directly into the endogenous class MHC antigen processing machinery. However, a limitation to targeting specific antigens limited to a relatively small subset of tumors is that mutations or overexpression of specific tumor associated antigens must be determined and applied on an individual basis.

An optimal immunotherapeutic strategy would allow treatment of a broad spectrum of human malignancies with a common pharmaceutical product. Stimulating immune responses to tumors with p53 mutations may enable treatment of a broad spectrum of tumors as approximately 50% of tumors have mutations in the p53 tumor suppresser gene. The p53 tumor associated antigen is characterized as a mutant TAA. Initially, strategies were designed to elicit CTL responses to "unique peptide antigens" generated by the p53 mutant sequences. This strategy was based on the premise that tumor specific CTL recognize peptides, derived from endogenously synthesized cellular proteins, presented by class I major histocompatibility complex (MHC) molecules. However, targeting such tissue-specific antigens may restrict immunotherapies to a very limited set of tumors as the mutations occur in many different loci within the p53 gene.

A distinguishing characteristic of p53 tumor associated antigens is that mutations within the p53 tumor associated antigen occur in approximately 50% of human malignancies. Moreover, most of the mutations result in an increase in the half-life of the p53 proteins resulting in a marked overexpression in tumor cells. The extended expression of p53 in tumor cells may modify processing and presentation of wt p53-derived peptides by MHC class I molecules. Since most MHC class I receptors are occupied by endogenously derived cellular proteins, a shift in p53 expression may result in a disproportionate number of MHC molecules presenting p53 derived peptides. This may permit development of T cell responses to p53 by T cells expressing T cell receptors (TCR) with low to moderate affinity. Indeed, several lines of evidence support the premise that tolerance to p53 can be overcome resulting in an immune response to tumor cells overexpressing p53. Anti-p53 antibodies have been found in sera of patients with several types of cancers and T cell lymphoproliferative responses to p53 have been detected in breast cell cancer patients. Moreover, subcutaneous immunization with canarypox viral vectors expressing p53 protected mice from challenge with tumors overexpressing p53.

Another distinguishing feature of utilizing p53 transgenes to stimulate tumor immunity is that transduction of tumors cells bearing p53 mutations with wt p53 transgenes generally induces apoptosis. Recent reports indicate that phagocytosis of apoptotic cells by dendritic cells may be an important mechanism for antigen transfer to dendritic cells and subsequent stimulation of specific T cell immunity to antigens expressed by the apoptotic cell. Thus, the induction of apoptosis may promote antigen loading of unknown TAA following phagocytosis by dendritic cells resulting in a more broad spectrum of tumor associated antigenic stimuli as described in the methods of use section below.

An important issue for strategies to induce immunity to self antigens that are differentially expressed in tumor cells is to assess the potential for autoimmune responses to normal cells. Several preclinical studies in mice induced to respond to p53 using peptide antigens and viral vectors have been reported in which specific cytotoxic T cell responses to tumor cells overexpressing p53 were observed while cells expressing normal levels of p53 were not killed. This has been attributed to the induction of T cell responses by CTL cells bearing T cell receptors (TCR) with low to moderate affinity for self MHC/p53 peptide complexes; T cells bearing TCR with high affinity are presumed to be eliminated during thymic negative selection. Moreover, in recent clinical trials, autoimmune responses were assessed in patients undergoing ex vivo dendritic cell immunotherapy to induce immune responses to melanoma antigens. Specific responses to melanoma antigens were successfully induced in the patients, yet no clinically overt sign of autoimmunity were observed.

Genetic immunization has proven to be an effective means to stimulate CTL mediated immunity to viruses and tumors. Expression of transgenes or minigenes (encoding antigenic peptides) intracellularly results in delivery of the immunogen directly into the MHC class I peptide processing and antigen loading system. Moreover, the entire antigenic protein or multiple proteins can be expressed allowing natural processing and loading of the antigenic peptides onto numerous allelic MHC class I and class II molecules permitting a more broad immune response. DNA vaccines and viral vectors show significant promise as effective vehicles for genetic immunization.

In vivo CTL activation may be mediated by dendritic cells. Dendritic cells are professional antigen presenting cells. Dendritic cells exist in distinct functional states. Immature dendritic cells corresponding to those found in peripheral tissues, exhibit a phenotype in which most class II molecules are intracellular and localized to lysosomes. In this phase, they are capable of uptake of antigen. These immature dendritic cells "patrol" the peripheral tissues in search of foreign antigens. Culturing dendritic cell precursors in vitro with GM-CSF and IL-4 induces differentiation into immature dendritic cells capable of highly efficient antigen uptake. Further differentiation into mature DC with highly developed antigen presentation functions can be induced by CD40 ligation, TNFα or LPS. Moreover, antigen pulsed dendritic cells under these culture conditions are extremely efficient at stimulating lymphoproliferative and CTL responses both in vitro and in vivo (Current estimates indicate that dendritic cells may be 10–100 times more potent as antigen presenting cells than other APCs such as macrophage and B cells). These immature dendritic cells mature into an intermediate phenotype in which intracellular class II molecules are found in peripheral non-lysosomal vesicles. The intermediate cells then differentiate into late dendritic cells which express almost all of their class II molecules on the plasma membrane. The maturing dendritic cells migrate to the lymph nodes where they present the processed peptides to T-cells.

The ability of dendritic cells to present tumor antigens to the immune system to recruit an immune response to tumor cells has been suggested as an anticancer therapy. The majority of dendritic cell therapeutic studies to date have utilized ex vivo strategies to load dendritic cells with antigen and to activate them to stimulate T cell immunity following reinfusion. The antigen pulsed dendritic cells are then reinfused into the hosts by various different routes to stimulate tumor specific T cell immunity. One advantage of ex vivo dendritic cell therapeutic strategies is the broader capacity to charge dendritic cells with various forms of antigen in vitro in manners not feasibly done in vivo (i.e., pulsing with recombinant protein antigens, tumor cell lysates or even tumor RNA extracts). This suggests that dendritic cells may be special in their capacity to process antigens using alternative antigen processing systems. Genetic methods using various viral vectors have also been successfully utilized to transduce dendritic cells with transgenes encoding tumor associated antigens or minigenes encoding MHC restricted peptide sequences.

A preferred strategy would be to induce direct in vivo stimulation of dendritic cells to induce strong tumor immunity and the preferred procedures in this invention utilize strategies to stimulate dendritic cell mediated immunotherapy in vivo. Genetic antigen delivery systems are well suited for in vivo strategies. However the use of genetic adjuvants such as cytokines, to mobilize dendritic cells and induce differentiation and activation, as well as chemokines to direct immature dendritic cells to the tumor site and mature dendritic cells to the lymph nodes may be essential to achieve consistently effective anti-tumor immunity and regression. The invention described herein are designed to effectively induce strong inflammatory responses mediated by dendritic cells within the tumor to enable the immune response to overcome the natural tolerance mechanisms utilized be tumors to evade immune surveillance and or clearance of tumors.

SUMMARY OF THE INVENTION

The present invention provides compositions which are engineered to induce killing of tumor cells and concomitantly mobilize differentiate, activate and attract dendritic cells through the expression of cytokines and dendritic cell chemoattractants. This combination therapy is called p53 adjunctive immunotherapy. This invention is designed to effectively induce multiple stages of dendritic cell differentiation, activation and migration in vivo using gene therapy delivery systems. First, recruitment of immature dendritic cells (that efficiently phagocytose and process tumor antigens) to the site of the tumor. Second, promote activation and migration of the dendritic cells to regional lymph nodes where the activated dendritic cells can stimulate tumor specific T cells and overcome tolerance to stimulated strong tumor immunity. The transduction of tumor cells with p53 is designed to reduce the primary tumor mass via cell cycle arrest and apoptosis as well as to promote antigen transfer of unknown or cryptic tumor antigens to dendritic cells by means of phagocytosis of the apoptotic tumor cells. Thus, providing a means to generate diverse immune responses to a broad spectrum of multiple tumor associated antigen, which may be essential for effective tumor immunity to heterogeneous tumor cells in the primary tumor and distal metastases. Moreover, this invention describes the rational design of utilizing viral vectors (preferred vector is rAd) for multiple administrations of targeted delivery to dendritic cells which can promote differentiation and activation of the transduced dendritic cells (thus augmenting in vivo stimulation of T cells, NK cells and B cells. The present invention provides a method to induce an anti-tumor immune response through the use of such compositions.

DETAILED DESCRIPTION OF THE INVENTION

The present invention provides expression vectors encoding a cytotoxic transgene and a dendritic cell chemoattractant. The vectors of the present invention may optionally encode a cytokine gene. The term "expression vector" refers to viral and non-viral vectors comprising a transgene expression cassette. The term "expression cassette" is used herein to define a nucleotide sequence containing regulatory elements operably linked to transgene coding sequence so as to result in the transcription and translation of a transgene in a cell. The term "regulatory element" refers to promoters, enhancers, transcription terminators, polyadenylation sites, and the like. The expression cassette may also contain other sequences aiding expression and/or secretion of the therapeutic gene The regulatory elements may be arranged so as to allow, enhance or facilitate expression of the transgene only in a particular cell type. For example, the expression cassette may be designed so that the transgene is under control of an inducible promoter, tissue specific or tumor specific promoter, or temporal promoter.

The term "operably linked" refers to a linkage of polynucleotide elements in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleotide sequences being linked are typically contiguous. However, as enhancers generally function when separated from the promoter by several kilobases and intronic seqences may be of variable lengths, some polynucleotide elements may be operably linked but not directly flanked and may even function in trans from a different allele or chromosome.

The term "inducible promoter" refers to promoters which facilitate transcription of the therapeutic transgene preferably (or solely) under certain conditions and/or in response to external chemical or other stimuli. Examples of inducible promoters are known in the scientific literature (See, e.g. Yoshida and Hamada (1997) Biochem. Biophys. Res. Comm. 230:426–430; Iida, et al. (1996) J. Virol. 70(9):6054–6059; Hwang, et al. (1997) J. Virol 71(9):7128–7131; Lee, et al. (1997) Mol. Cell. Biol. 17(9):5097–5105; and Dreher, et al. (1997) J. Biol. Chem. 272(46); 29364–29371. Examples of radiation inducible promoters include the EGR-1 promoter. Boothman, et al.(1994) volume 138 supplement pages S68–S71.

Tissue specific and tumor specific promoters are well known in the art and include promoters active preferentially in smooth muscle (α-actin promoter), pancreas specific (Palmiter, et al.(1987) Cell 50:435), liver specific Rovet, et al. (1992) J. Biol. Chem. 267:20765; Lemaigne, et al. (1993) J. Biol. Chem. 268:19896; Nitsch, et al. (1993) Mol. Cell. Biol. 13:4494), stomach specific (Kovarik, et al. (1993) J. Biol. Chem. 268:9917, pituitary specific (Rhodes, et al. (1993) Genes Dev. 7:913, prostate specific (U.S. Pat. No. 5,698,443, Henderson, et. al. issued Dec. 16, 1997), etc.

The term "temporal promoters" refers to promoters which drive transcription or the therapeutic transgene at a point later in the viral cycle relative to the promoter controlling expression of the response element and are used in conjunction with viral vector systems. Examples of such temporally regulated promoters include the adenovirus major late promoter (MLP), other late promoters. For herpes simplex viruses, the an examples of temporal promoter include the latent activated promoters.

The term "non-viral vector" refers to an autonomously replicating, extrachromosomal circular DNA molecules, distinct from the normal genome and nonessential for cell survival under non-selective conditions capable of effecting the expression of a DNA sequence in the target cell. Plasmids autonomously replicate in bacteria to facilitate bacterial production, but it is not necessary that such plasmids containing the cyclin dependent kinase gene replicate in the target cell in order to achieve the therapeutic effect. Additional genes, such as those encoding drug resistance, can be included to allow selection or screening for the presence of the recombinant vector. Such additional genes can include, for example, genes encoding neomycin resistance, multidrug resistance, thymidine kinase, β-galactosidase, dihydrofolate reductase (DHFR), and chloramphenicol acetyl transferase.

In order to insure efficient delivery of the therapeutic gene to a particular tissue or organ, it may be advantageous to incorporate elements into the non-viral delivery system which facilitate cellular targeting. For example, a lipid encapsulated expression plasmid may incorporate modified surface cell receptor ligands to facilitate targeting. Although a simple liposome formulation may be administered, the liposomes either filled or decorated with a desired composition of the invention of the invention can delivered systemically, or can be directed to a tissue of interest, where the liposomes then deliver the selected therapeutic/immunogenic peptide compositions. Examples of such ligands includes antibodies, monoclonal antibodies, humanized antibodies, single chain antibodies, chimeric antibodies or functional fragments (Fv, Fab, Fab') thereof. Alternatively, non-viral vectors can be linked through a polylysine moiety to a targeting moiety as described in Wu, et al. U.S. Pat. No. 5,166,320 issued Nov. 24, 1992 and Wu, et al, U.S. Pat. No. 5,635,383 issued Jun. 3, 1997, the entire teachings of which are herein incorporated by reference.

The terms "viral vector" and "virus" are used interchangeably herein to refer to any of the obligate intracellular parasites having no protein-synthesizing or energy-generating mechanism. The viral genome may be RNA or DNA contained with a coated structure of protein of a lipid membrane. The terms virus(es) and viral vector(s) are used interchangeably herein. The viruses useful in the practice of the present invention include recombinantly modified enveloped or non-enveloped DNA and RNA viruses, preferably selected from baculoviridiae, parvoviridiae, picornoviridiae, herpesviridiae, poxviridae, or adenoviridiae. The viruses may be naturally occurring viruses or their viral genomes may be modified by recombinant DNA techniques to include expression of exogenous transgenes and may be engineered to be replication deficient, conditionally replicating or replication competent. Chimeric viral vectors which exploit advantageous elements of each of the parent vector properties (See e.g., Feng, et al.(1997) Nature Biotechnology 15:866–870) may also be useful in the practice of the present invention. Minimal vector systems in which the viral backbone contains only the sequences need for packaging of the viral vector and may optionally include a transgene expression cassette may also be produced according to the practice of the present invention. Although it is generally favored to employ a virus from the species to be treated, in some instances it may be advantageous to use vectors derived from different species which possess favorable pathogenic features. For example, equine herpes virus vectors for human gene therapy are described in WO98/27216 published Aug. 5, 1998. The vectors are described as useful for the treatment of humans as the equine virus is not pathogenic to humans. Similarly, ovine adenoviral vectors may be used in human gene therapy as they are claimed to avoid the antibodies against the human adenoviral vectors. Such vectors are described in WO 97/06826 published Apr. 10, 1997.

The term "replication deficient" refers to vectors which are incapable of replication in a wild type mammalian cell. In order to produce such vectors in quantity, the producer cell line must be cotransfected with a helper virus or modified to complement the missing functions. E.g. 293 cells have been engineered to complement adenoviral E1 deletions allowing propagation of the E1 deleted replication deficient adenoviral vectors in 293 cells. The term "replication competent viral vectors" refers to a viral vector which is capable of infection, DNA replication, packaging and lysis of an infected cell. The term "conditionally replicating viral vectors" is used herein to refer to replication competent vectors which are designed to achieve selective expression in particular cell types while avoiding untoward broad spectrum infection. Such conditional replication may be achieved by operably linking tissue specific, tumor specific or cell type specific or other selectively induced regulatory control sequences to early genes (e.g. the E1 gene of adenoviral vectors).

Cell type specificity or cell type targeting may also be achieved in viral vectors derived from viruses having characteristically broad infectivities by the modification of the viral envelope proteins. For example, cell targeting has been achieved with adenovirus vectors by selective modification of the viral genome knob and fiber coding sequences to achieve expression of modified knob and fiber domains having specific interaction with unique cell surface receptors. Examples of such modifications are described in Wickham, et al.(1997) J. Virol 71(11):8221–8229 (incorporation of RGD peptides into adenoviral fiber proteins); Arnberg, et al.(1997) Virology 227:239–244 (modification of adenoviral fiber genes to achieve tropism to the eye and genital tract); Harris and Lemoine (1996) TIG 12(10):400–405; Stevenson, et al.(1997) J. Virol. 71(6) :4782–4790; Michael, et al.(1995) gene therapy 2:660–668 (incorporation of gastrin releasing peptide fragment into adenovirus fiber protein); and Ohno, et al.(1997) Nature Biotechnology 15:763–767 (incorporation of Protein A-IgG binding domain into Sindbis virus). Other methods of cell specific targeting have been achieved by the conjugation of antibodies or antibody fragments to the envelope proteins (see, e.g. Michael, et al. (1993) J. Biol. Chem 268:6866–6869, Watkins, et al. (1997) gene therapy 4:1004–1012; Douglas, et al.(1996) Nature Biotechnology 14: 1574–1578. Alternatively, particular moieties may be conjugated to the viral surface to achieve targeting (See, e.g. Nilson, et al. (1996) gene therapy 3:280–286 (conjugation of EGF to retroviral proteins). These targeting modifications may be introduced into the viral vectors of the present invention in addition to or in combination with other modifications to the viral genome. Targeting modifications may be used with replication deficient, replication competent or conditionally replicating viruses.

Alternatively, cell type targeting with viral vectors may be achieved through the use of a pathway responsive promoter driving a repressor of viral replication. The term "pathway-responsive promoter" refers to DNA sequences that bind a certain protein and cause nearby genes to respond transcriptionally to the binding of the protein in normal cells. Such promoters may be generated by incorporating response elements which are sequences to which transcription factors bind. Such responses are generally inductive,though there are several cases where increasing protein levels decrease transcription. Pathway-responsive promoters may be naturally occurring or synthetic. Pathway-responsive promoters are typically constructed in reference to the pathway or a functional protein which is targeted. For example, a naturally occurring p53 pathway-responsive promoter would include transcriptional control elements activated by the presence of functional p53 such as the p21 or bax promoter. Alternatively, synthetic promoters containing p53 binding sites upstream of a minimal promoter (e.g. the SV40 TATA box region) may be employed to create a synthetic pathway-responsive promoter. Synthetic pathway-responsive promoters are generally constructed from one or more copies of a sequence that matches a consensus binding motif. Such consensus DNA binding motifs can readily be determined. Such consensus sequences are generally arranged as a direct or head-to-tail repeat separated by a few base pairs. Elements that include head-to-head repeats are called palindromes or inverted repeats and those with tail-to-tail repeats are called everted repeats.

Examples of pathway-responsivepromoters useful in the practice of the present invention include synthetic insulin pathway-responsive promoters containing the consensus insulin binding sequence (Jacob, et al. (1995). J. Biol. Chem. 270:27773–27779), the cytokine pathway-responsive promoter, the glucocorticoid pathway-responsive promoter (Lange, et al.(1992) J Biol. Chem. 267:15673–80), IL1 and IL6 pathway-responsive promoters (Won K.-A and Baumann H. (1990) Mol.Cell.Biol. 10: 3965–3978), T3 pathway-responsive promoters, thyroid hormone pathway-responsive promoters containing the consensus motif: 5' AGGTCA 3.', the TPA pathway-responsive promoters (TREs), TGF-β pathway-responsive promoters (as described in Grotendorst, et al.(1996) Cell Growth and Differentiation 7: 469–480). Additionally, natural or synthetic E2F pathway responsive promoters may be used. An example of an E2F pathway responsive promoter is described in Parr, et al. (1997, Nature Medicine 3:1145–1149) which describes an E2F-1 promoter containing 4 E2F binding sites and is reportedly active in tumor cells with rapid cycling. Examples of other pathway-responsive promoters are well known in the art and can be identified in the Database of Transcription Regulatory Regions on Eukaryotic Genomes accessible through the internet at http://www.eimb.rssi.ru/TRRD.

In the preferred practice of the invention as exemplified herein, the vector comprises a synthetic TGF-β pathway-responsive promoter active in the presence of a functional TGF-β pathway such as the promoter containing SRE and PAI pathway responsive promoters. PAI refers to a synthetic TGF-β pathway-responsive promoter comprising sequences responsive to TGF-β signally isolated from the plasmninogen activator-I promoter region. The PAI-pathway-responsive promoter may be isolated as a 749 base pair fragment isolatable from the plasmid p800luc (as described in Zonneveld, et al. (1988) PNAS 85:5525–5529 and available from GenBank under accession number J03836). SRE refers to a synthetic TGF-β response element comprising a repeat of 4 of the Smad-4 DNA binding sequences (GTCTAGAC as described in Zawel, et al. (1988) Mol. Cell 1:611–617. The SRE response element may be generated by annealing complimentary oligonucleotides encoding the Smad-4 binding sequences and cloning in plasmid pGL#3-promoter luciferase vector (commercially available from ProMega).

Similarly, a "p53 pathway-responsive promoter" refers to a transcriptional control element active in the presence of a functional p53 pathway. The p53 pathway-responsive promoter may be a naturally occurring transcriptional control region active in the presence of a functional p53 pathway such as the p21 or mdm2 promoter. Alternatively, the p53 pathway-responsive promoter may be a synthetic transcriptional control region active in the presence of a functional p53 pathway such as the SRE and PAI-RE pathway-responsive promoters. p53-CON describes a p53 pathway-responsive promoter containing a synthetic p53 response element constructed by insertion of two synthetic p53 consensus DNA binding sequences (as described in Funk, et al. (1992) Mol.Cell Biol. 12:2866–2871) upstream of the SV40 TATA box. RGC refers to a synthetic p53 pathway-responsive promoter using a tandem of the p53 binding domains identified in the ribosomal gene cluster. p53CON and RGC response elements can be constructed by annealing complementary oligonucleotides and p53 responsive promoters can be constructed by cloning in plasmid pGL3-promoter luciferase vector (commercially available from ProMega). The cell type specific (tissue specific, tumor specific, pathway specific, cell cycle regulatory promoter) promoter or inducible promoter may be used in lieu of the native early gene promoter region in the vectors of the present invention to provide preferential expression in particular cell types.

Alternatively, the one may use a pathway responsive promoter to drive expression of a repressor of viral replication. The term "repressor of viral replication" refers to a protein, if expressed in a given cell, substantially represses viral replication. In the case of adenoviral vectors, the E2F-Rb fusion construct as described in European Patent Application No. 94108445.1 published Dec. 6, 1995 (Publication number. 0 685 493 A1) may be employed. E2F-Rb fusion protein consists of the DNA binding and DP1 heterodimerization domains of the human E2F-2 transcription factor protein (amino acids 95–286 of wild type E2F) fused to the Rb growth suppression domain (amino acids 379–928 of the wild type Rb protein). The E2F-Rb fusion protein is a potent repressor of E2F transcription and arrests cells in G1. The DNA binding domain is located at amino acids 128–193 and the dimerization domain is located at 194–289. The sequence of the human E2F2 protein is available from GenBank under accession number 2494288 deposited Nov. 1, 1997 as updated Jul. 15, 1998.

In the preferred practice of the invention, the viral vector is an adenovirus. The term "adenovirus" is synonomous with the term "adenoviral vector" and refers to viruses of the genus adenoviridiae. The term adenoviridiae refers collectively to animal adenoviruses of the genus mastadenovirus including but no limited to human, bovine, ovine, equine, canine, porcine, murine and simian adenovirus subgenera. In particular, human adenoviruses includes the A-F sugenera as well as the individual serotypes thereof the individual serotypes and A-F subgenera including but not limited to human adenovirus types 1, 2, 3, 4, 4a, 5, 6, 7, 8, 9, 10, 11 (Ad11A and Ad 11P), 12, 13,14,15,16,17,18,19, 19a, 20, 21, 22, 23, 24, 25, 26, 27, 28, 29, 30, 31, 32, 33, 34, 34a, 35, 35p, 36, 37, 38, 39, 40, 41, 42, 43, 44, 45, 46, 47, 48, and 91. The term bovine adenoviruses includes but is not limited to bovine adenovirus types 1,2,3,4,7, and 10. The term canine adenoviruses includes but is not limited to canine types 1 (strains CLL, Glaxo, RI261, Utrect, Toronto 26-61) and 2. The term equine adenoviruses includes but is not limited to equine types 1 and 2. The term porcine adenoviruses includes but is not limited to porcine types 3 and 4. The term viral vector includes replication deficient, replication competent and conditionally replicating viral vectors.

More preferred are vectors derived from human adenovirus types 2 and 5. These vectors may incorporate particular modifications to enhance their therapeutic potential. For example they may include deletions of E1a and E1b genes. Certain other regions may be enhanced or deleted to provide specific features. For example upregulation of the E3 region is described to reduce the immunogenicity associated with human adenoviral vectors administered to human subjects. The E4 region has been implicated as important to expression of transgenes from the CMV promoter, however the E4orf 6 protein has been described as leading to the degradation of p53 in target cells in the presence of E1b large protein. Steegenga, et al. (1998) Oncogene 16:345–347. Consequently, the elimination of such sequences from p53 gene therapy using adenoviral vectors is preferred.

In the preferred practice of the invention when using the vectors of the present invention to treat diseases associated with uncontrolled cellular proliferation, it is preferred that an adenoviral vector be employed containing specific deletions in the E1A region so as to reduce the ability of the E1a gene product to bind to the p300 and Rb proteins while retaining the transactivating function of the E1a CR3 domain. The vectors of the present contain deletions in the E1a coding sequence to eliminate p300 and p105-Rb binding sites in the 13S coding sequence. In the preferred practice of the invention, the p300 binding deletions are represented by deletions of amino acids from about 4 to about 25 or from about 36 to about 49. In the preferred practice of the invention, the Rb binding deletions are represented by elimination of amino acids from about 111–127, preferably from about 111–123. More preferred is a vector wherein said deletion in the E1a-p300 binding domain comprises a deletion of the codons for amino acids 4 to 25 of the adenoviral E1a gene product. More preferred is a vector wherein deletion in the E1a-Rb binding domain comprises a deletion of the codons for amino acids 111–123 of the adenoviral E1a gene product. Alternatively, pRb binding may be eliminated by the introduction of a mutation to eliminate amino acids 124–127 of the E1A 289R and 243R proteins. In the most preferred embodiment of the present invention as exemplified herein the vector comprises a deletion of amino acids 4–25 and 111–123 of the E1a 13S gene product.

Additionally, the elimination of amino acids from approximately 219 to 289 of the E1a 289R protein and 173 to 243 of the E1A 243R protein may be introduced. For example, by introducing a point mutation at position corresponding to position 1131 of the human Ad5 genome (i.e., changing the cytosine$^{1131}$ to a guanine) creates a stop codon. This mutation results in the elimination of amino acids 219 to 289 of the E1a 289R protein and 173 to 243 of the E1A 243R protein. This mutation is made optionally in addition to the deletions in Rb and p300 binding described above. Additional examples of such parent vectors are described in co-pending U.S. Patent Application Serial Nos. 60/104,317 and 08/09/172,684 filed Oct. 15, 1998.

The term "cytotoxic transgene" refers to a nucleotide sequence the expression of which in the target cell induces lysis or apoptosis of the cell. The term cytotoxic transgene includes but is not limited to tumor suppressor genes, toxin genes, cytostatic genes, pro-drug activating genes, or apoptotic genes. The vectors of the present invention may be used to produce one or more therapeutic transgenes, either in tandem through the use of IRES elements or through independently regulated promoters.

The term "tumor suppressor gene" refers to a nucleotide sequence, the expression of which in the target cell is capable of suppressing the neoplastic phenotype and/or inducing apoptosis. Examples of tumor suppressor genes useful in the practice of the present invention include the p53 gene, the APC gene, the DPC-4 gene, the BRCA-1 gene, the BRCA-2 gene, the WT-1 gene, the retinoblastoma gene (Lee, et al. (1987) Nature 329:642), the MMAC-1 gene, the adenomatous polyposis coli protein (Albertsen, et al., U.S. Pat. No. 5,783,666 issued Jul. 21, 1998), the deleted in colon carcinoma (DCC) gene, the MMSC-2 gene, the NF-1 gene, nasopharyngeal carcinoma tumor suppressor gene that maps at chromosome 3p21.3. (Cheng, et al. 1998. Proc. Nat. Acad. Sci. 95:3042–3047), the MTS1 gene, the CDK4 gene, the NF-1 gene, the NF2 gene, and the VHL gene.

The term "toxin gene" refers to nucleotide sequence, the expression of which in a cell produces a toxic effect. Examples of such toxin genes include nucleotide sequences encoding pseudomonas exotoxin, ricin toxin, diptheria toxin, and the like.

The term "pro-apoptotic gene" refers to a nucleotide sequence, the expression thereof results in the programmed cell death of the cell. Examples of pro-apoptotic genes include p53, adenovirus E3-11.6K, the adenovirus E4orf4 gene, p53 pathway genes, and genes encoding the caspases.

The term "pro-drug activating genes" refers to nucleotide sequences, the expression of which, results in the production of protein capable of converting a non-therapeutic compound into a therapeutic compound, which renders the cell susceptible to killing by external factors or causes a toxic condition in the cell. An example of a prodrug activating gene is the cytosine deaminase gene. Cytosine deaminase converts 5-fluorocytosine to 5-fluorouracil, a potent antitumor agent). The lysis of the tumor cell provides a localized burst of cytosine deaminase capable of converting 5FC to 5FU at the localized point of the tumor resulting in the killing of many surrounding tumor cells. This results in the killing of a large number of tumor cells without the necessity of infecting these cells with an adenovirus (the so-called bystander effect"). Additionally, the thymidine kinase (TK) gene (see e.g. Woo, et al. U.S. Pat. No. 5,631,236 issued May 20, 1997 and Freeman, et al. U.S. Pat. No. 5,601,818 issued Feb. 11, 1997) in which the cells expressing the TK gene product are susceptible to selective killing by the administration of gancyclovir may be employed.

The term "cytokine gene" refers to a nucleotide sequence, the expression of which in a cell produces a cytokine. Examples of such cytokines include GM-CSF, the interleukins, especially IL-1, IL-2, IL-4, IL-12, IL-10, IL-19, IL-20, interferons of the $\alpha$, $\beta$ and gamma subtypes especially interferon $\alpha$-2b and fusions such as interferon $\alpha$-2$\alpha$-1.

It will be readily apparent to those of skill in the art that modifications and or deletions to the above referenced genes so as to encode functional subfragments of the wild type protein may be readily adapted for use in the practice of the present invention. For example, the reference to the p53 gene includes not only the wild type protein but alos modified p53 proteins. Examples of such modified p53 proteins include modifications to p53 to increase nuclear retention, deletions such as the delta13–19 amino acids to eliminate the calpain consensus cleavage site, modifications to the oligomerization domains (as described in Bracco, et al. PCT published application WO97/0492 or U.S. Pat. No. 5,573,925).

It will be readily apparent to those of skill in the art that the above cytotoxic genes may be secreted into the media or localized to particular intracellular locations by inclusion of a targeting moiety such as a signal peptide or nuclear localization signal (NLS). Also included in the definition of therapeutic transgene are fusion proteins of the therapeutic transgene with the herpes simplex virus type 1 (HSV-1) structural protein, VP22. Fusion proteins containing the VP22 signal, when synthesized in an infected cell, are exported out of the infected cell and efficiently enter surrounding non-infected cells to a diameter of approximately 16 cells wide. This system is particularly useful in conjunction with transcriptionally active proteins (e.g. p53) as the fusion proteins are efficiently transported to the nuclei of the surrounding cells. See, e.g.Elliott, G. & O'Hare, P. Cell. 88:223–233:1997; Marshall, A. & Castellino, A. Research News Briefs. Nature Biotechnology. 15:205:1997; O'Hare, et al. PCT publication WO97/05265 published Feb. 13, 1997. A similar targeting moiety derived from the HIV Tat protein is also described in Vives, et al. (1997) J. Biol. Chem. 272:16010–16017.

The term "dendritic cell chemoattractants" (DCC) refers to chemotactic chemokines capable of attracting and/or directing the migration of dendritic cells to a particular location. It has been demonstrated that certain chemokines, fMLP (representative of formyl peptides of bacterial origin), C5a and the C-C chemokines monocyte chemotactic protein (MCP)-3, macrophage inflammatory protein (MIP)-1 $\alpha$/LD78, MIP-1 $\beta$, MIP-3 $\alpha$, MIP-3$\beta$, 6-CKINE, and RANTES, have been involved in the recruitment and chemotactic migration of dendritic cells. Sozzani, et al. (1995) J. Immunol. 1995 155(7):3292–5. Xu, et al.suggest that all C-C chemokines, including MCP-1, MCP-2, MCP-3, MIP1 $\alpha$, MIP-1$\beta$, and RANTES, induced migration of DC-enriched cells cultured with or without IL-4. Xu, et al. (1996) J. Leukoc. Biol. 60(3):365–71. Greaves, et al. (1997) J. Exp. Med. 186(6):837–44, indicate that MIP-3-$\alpha$ specifically interacts with the CC chemokine receptor 6 expressed on dendritic cells capable of directing migration of dendritic cells. Moreover, recent evidence demonstrates that MIP-3$\alpha$ induced chemotaxis of immature dendritic cells, whereas, MIP-3$\beta$ induced chemotaxis of mature dendritic cells. Thus, providing a means to regulate migration of immature dendritic cells to sites of inflammation (i.e., tumors) and mature dendritic cells to lymph nodes where the activated dendritic cells can stimulate T cell responses. The dendritic cell chemoattractant may be expressed in and intracellular form where it is released upon cell lysis or in secreted form by the use of a signal peptide. In the preferred practice of the invention, the dendritic cell chemoattractant is selected from the group consisting of MIP-3-$\alpha$, macrophage inflammatory protein (MIP)-1 $\alpha$/LD78, and MIP 3$\beta$ to induce migration to the lymph nodes. In the most preferred practice of the invention, the dendritic cell chemoattractant is MIP-3-$\alpha$.

The present invention further provides a method of inducing an antitumor CTL immune response in a mammalian organism using p53 adjunctive immunotherapy in which co-transduction of tumor cells with p53, GM-CSF, IL-4 and chemokines (i.e., MIP-1$\alpha$) is done. Primary immunity to p53 is induced by coincidental transduction of dermal dendritic cells populations by intradermal/subcutaneous administration. The transduction of dendritic cells in the dermis is designed to ellicit efficient activation of T cells as viral vector administration in the dermis has been demonstrated be be highly effective for the induction of dendritic cell mediated activation of T cells. The transduction of tumor cells with p53 is designed to induce cell cycle arrest and apoptosis of tumor cells resulting in primary tumor mass reduction and to augment antigen transfer of cryptic or known tumor antigens to dendritic cells which are induced to migrate to the tumor by the cytokines and/or chemokines expressed in the tumor. This induces a strong primary response to p53 overexpression in tumor cells and then a diverse T cell response to a broad spectrum tumor associated antigens through antigen transfer of apoptotic tumor cells to dendritic cells migrating to the tumor. Such diversity of immunity is essential to induce clearance of heterogenous populations of tumor cells in the primary tumor mass and metastases which would otherwise be selected for mutant cells which lack expression of p53 or other single tumor associated antigens.

The transduction of tumor cells with GM-CSF and IL-4 induces the mobilization and differentiation of dendritic cells as well as to promote dendritic cell migration to the tumor. Moreover, the use of transient or regulated expression of IL-4 in the tumor may promote dendritic cells to remain in the immature state for a more extended period allowing for more antigen uptake befor the cells are induced to mature. The transduction of tumor cells with MIP-1 $\alpha$ is designed to promote chemotaxis and migration of immature dendritic cells to the tumor site. This strategy is designed to have the acummulative effect of inducing dendritic cell activation of peripheral dendritic cells in the dermis which can then be induced (along with de novo derived dendritic cells induced by GM-CSF and IL-4) to migrate to the tumor (induced by GM-CSF, IL-4 and/or MIP-1$\alpha$) where the dendritic cells can encounter apoptotic tumor cells (induced by p53) and phagocytose the apoptotic cells to elicit antigen transfer. Upon activation, the dendritic cells will then migrate to the draining lymph nodes and stimulate tumor specific T cell responses as well as NK cell responses and other cellular responses. Migration of mature dendritic cells to the lymph nodes can be augmented by transduction of lymph node cells (via intranodal injection) with vectors which induce expression of MIP-3$\beta$.

The term "mammalian organism" includes, but is not limited to, humans, pigs, horses, cattle, dogs, cats. Preferably one employs an adenoviral vector endogenous to the mammalian type being treated. Although it is generally favored to employ a virus from the species to be treated, in some instances it may be advantageous to use vectors derived from different species which possess favorable pathogenic features. For example, it is reported (WO 97/06826 published Apr. 10, 1997) that ovine adenoviral vectors may be used in human gene therapy to minimize the immune response characteristic of human adenoviral vectors. By minimizing the initial immune response, rapid systemic clearance of the vector is avoided resulting in a greater duration of action of the vector. However, later immune response is favored.

The term "neoplastic cell" is a cell displaying an aberrant growth phenotype characterized by independence of normal cellular growth controls. As neoplastic cells are not necessarily replicating at any given time point, the term neoplastic cells comprise cells which may be actively replicating or in a temporary non-replicative resting state (G1 or G0). Localized populations of neoplastic cells are referred to as neoplasms. Neoplasms may be malignant or benign. Malignant neoplasms are also referred to as cancers. The term cancer is used interchangeably herein with the term tumor. Neoplastic transformation refers the conversion of a normal cell into a neoplastic cell, often a tumor cell The present invention further provides a means to induce booster immunizations specifically targeted to antigen presenting cells which express Fc receptors including, in particular, dendritic cells. This method takes advantage of the fact that administration of rAd vectors into mammals induces a vigorous immune response, including humoral antibody responses and cellular T cell responses, to adenoviral proteins. The humoral response normally presents a problem for re-administration of rAd vectors to tissues such as the liver or lungs as the serum antibodies instantaneously bind the rAd particles upon repeated injection of the vector resulting in clearance. One of the primary mechanisms for antibody mediated viral clearance is to promote uptake by antigen presenting cells following binding of the Fc portion of the antibodies (which "coat" the viral particle capsids) via Fc-receptors (a process known as opsinization). These Fc-receptors are expressed on most antigen presenting cells including macrophages, B cells and dendritic cells. Henceforth, this mechanism can be utilized to specically target re-administration of rAd vectors engineered to induce transgene expression in antigen presenting cells such as macrophages and dendritic cells.

The present invention provides a method to target tumor associated antigens, chemokine receptors, chemokines and/ or cytokines to macrophages, dendritic cells and other Fc-receptor expressing cells following multiple administrations including intravenous, intraperitoneal, intravesicular and subcutaneous injection. Targeted delivery achieved by promoting antibody binding to the surface antigens on viral vectors. The antibody coated viral particles are targeted for uptake by antigen presenting cells such as macrophages and dendritic cells. Following internalization into endosomes, the pH within the endosome will become acidic. The acidic microenvironment within the endosomes and endolysosomes induces two essential functions which promotes successful transduction (including transgene expression) by rAd vectors (as well as other viral vectors). Namely, the acidic environment induces dissociation of the antibodies from the viral surface (thus exposing viral proteins utilized to escape the endosome) and the acidic pH promotes escape from the endosome (P. L. Leopold et. al., 1998, *Human Gene Therapy* 9:367–378). Following endosomal escape the rAd vector translocates to the nucleus and delivery the recombinant nucleotide sequence into the nucleus resulting in multiple rounds of antigen presenting cell targeted expression of therapeutic transgenes. The transduced antigen presenting cells then activate T cells, NK cells, B cells, etcetera to augment anti-tumor immunity.

Dendritic cells have been demonstrated to take up many different bacterial and viral particles. Depending on the particular micro-organism, dendritic cells have been demonstrated to be induced to differentiate and to become activated or to be suppressed with respect to the functional capacity to stimulate antigen specific lymphocytes. For example, the influenza virus PR8 induces differentiation and activation of dendritic cells following infection. Whereas, measles virus induces a suppression of dendritic cell antigen presentation functions upon infection. We have discovered that rAd vectors can induce differentiation of dendritic cells from blood monocytes to immature dendritic cells and activation of immature dendritic cells to mature dendritic cells independent of exogenous cytokines and independent of the transgene. Levels of endotoxin in the purified vector preparations were well below the LPS dose required to induce dendritic cell activation (Verhasselt V et.al., Mar. 15, 1997 J Immunol;158(6):2919–25).

Figure 1:
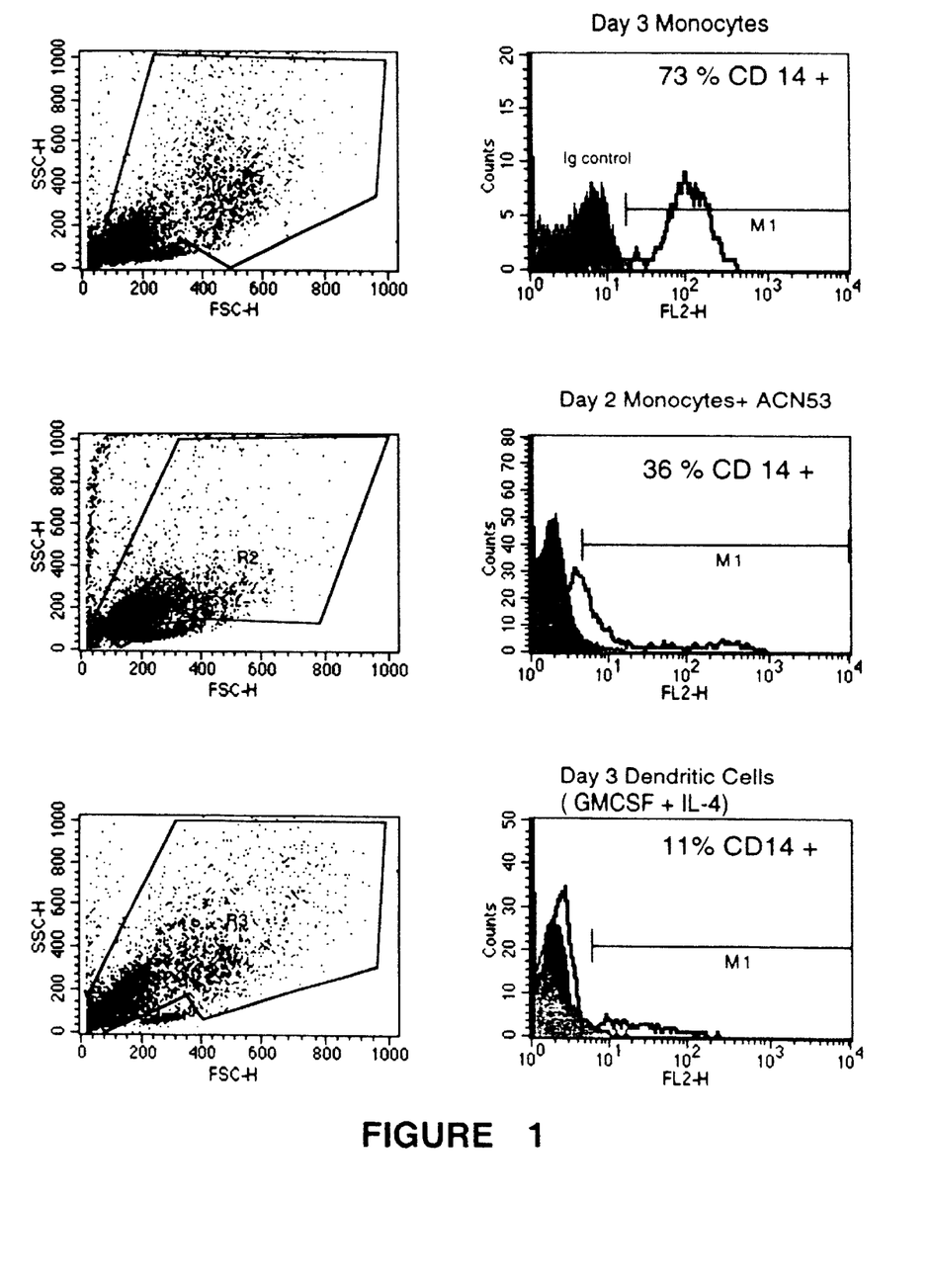
FIG. 1 presents the flow cytometric data demonstrating differentiation of CD14+ blood monocytes to CD14-negative immature DC following transduction of blood monocytes within 3 days. Day 3 cultured monocytes expressed high levels of CD14 (indicative of monocytes), whereas, transduced monocytes or monocytes co-cultured with IL4 and GM-CSF downmodulated CD14 (indicative of immature dendritic cells).

The flow cytometric data in FIG. 1 demonstrates that rAd/p53 vectors induced differentiation of CD14+ blood monocytes to CD14-negative immature DC following transduction of blood monocytes within 3 days. As shown in FIG. 1, day 3 cultured monocytes expressed high levels of CD14 (indicative of monocytes), whereas, transduced monocytes or monocytes co-cultured with IL4 and GM-CSF down-modulated CD14 (indicative of immature dendritic cells. This result was achievable with two other vectors as well; namely rAd/empty and rAd/green fluorescent protein. Thus, this cytokine independent induction of differentiation of monocytes to immature dendritic cells was specifically induced by the rAd vector in a transgene independent manner.

Figure 2:
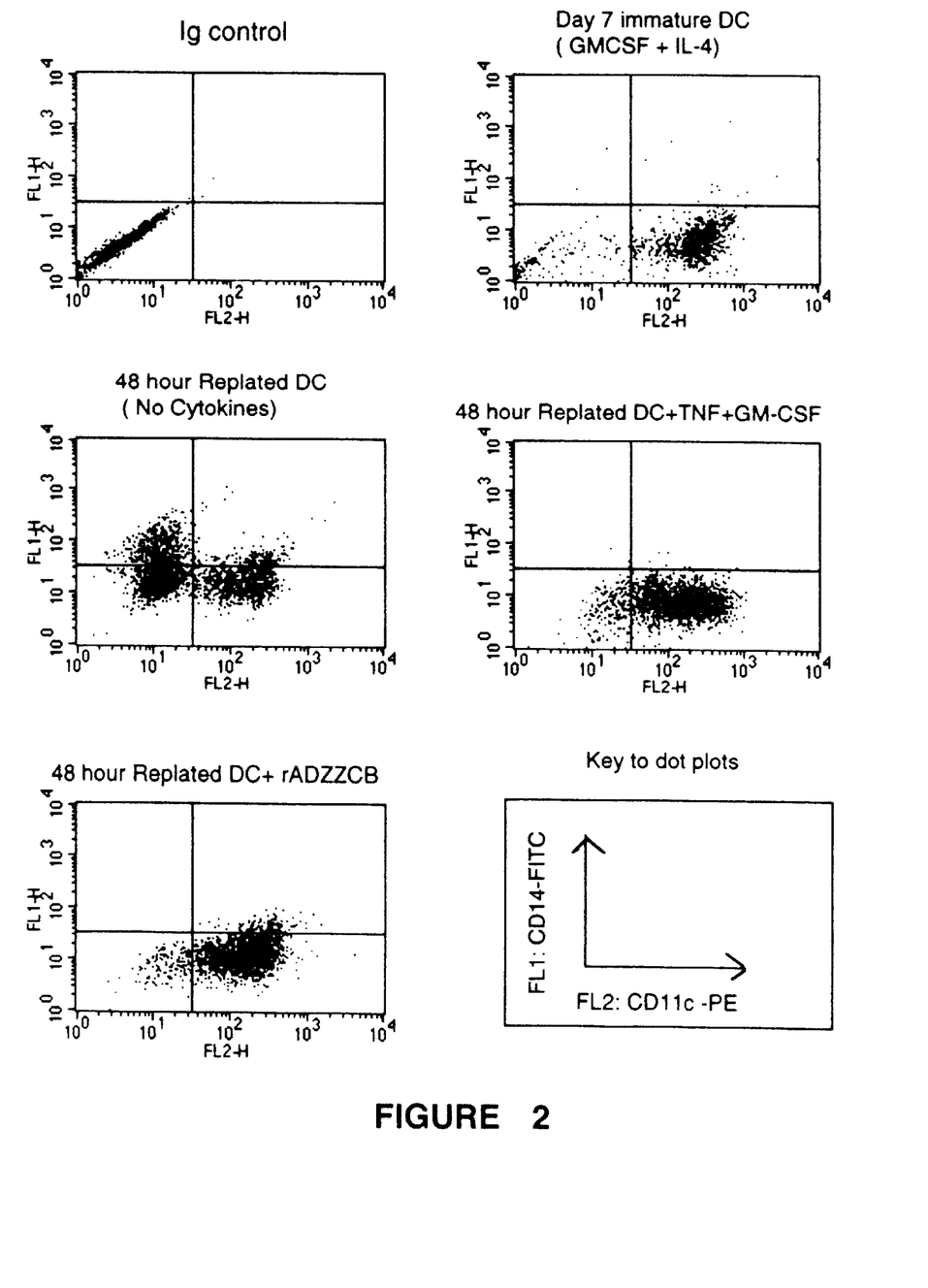
FIG. 2 presents the flow cytometric data demonstrating that rAd transduction of immature dendritic cells further induced maturation and activation of immature DC to mature DC independent of exogenous cytokine. Immature dendritic cells (cultured 5 days in GM-CSF and IL-4) de-differentiated back to CD14+ cells and lost expression of CD11c; indicative of monocytes following removal of cytokines and replating.

The flow cytometric data in FIG. 2 demonstrates that rAd transduction of immature dendritic cells further induced maturation and activation of immature DC to mature DC independent of exogenous cytokine. As shown in FIG. 2, immature dendritic cells (cultured 5 days in GM-CSF and IL-4) de-differentiated back to CD14+ cells and lost expression of CD11c; indicative of monocytes following removal of cytockines and replating. In contrast both rAd transduced cells and cells cultured weth TNFα (to induce differentiation to mature DC) retained expression of CD11c and were CD14 negative. Moreover, the cells induced to differentiate with either rAd or TNFa lost the capacity to uptake dextran indicative of mature DC (data not shown).

Thus, rAd vectors have the capacity to directly promote dendritic cell differentiation and activation. Consequently, rAd vectors are optimally suited for use as a gene therapy delivery vector for dendritic cell transduction for immunotherapy to induce strong T cell immunity. Although, the preferred procedures for this invention apply to the use of rAd vectors to induce enhanced dendritic cell immunotherapy, this process may also be applied to other viral vector systems and to certain non-viral systems. This provides a broad spectrum activation of T cells, B cells, NK cells, as well as other immune cells.

We also observed an apparent p53 transgene specific induction of apoptosis of dendritic following extended culture (five to seven days). Monocytes were induced to differentiate into immature dendritic cells by transduction with rAd/empty, rAd/green fluorescence protein or rAd/p53 by 3 days in culture. Remarkably, by five to seven days in culture, immature dendritic cells that had been transduced with rAd/p53, but not with rAd/empty or rAd/green fluorescence protein dissappeared. These results indicate that p53 overexpression in differentiating dendritic cells may induce apoptosis. This observation is important as dendritic cell phagocytosis (and/or other means of uptake) of apoptotic cells (particularly but not exclusively apoptotic dendritic cells) may be the optimal means for antigen uptake and presentation. The present invention provides a means to optimize gene based delivery of tumor or viral antigens to dendritic cells by delivering p53 to dendritic cells directly as well as indirectly via antigen transfer from the resulting apoptotic dendritic cell to subsequent dendritic cells. This process also provides the means to amplify the immunizing dose of tumor associated antigen transgenes as multiple dendritic cells may take up numerous apoptotic bodies from a single apoptotic dendritic cell transduced with p53. Moreover, this p53 induced apoptosis of dendritic cell can be utilized to amplify antigen presentation of any other tumor associated antigen transgene. That is to say, co-transduction of dendritic cells of p53 (to induce apoptosis) with a given tumor associated antigen (e.g., MAGE, CEA) induces antigen transfer of the other tumor associated antigen to many dendritic cells.

This invention facilitates the capacity to induce dendritic cell mediated immunotherapy in vivo. Although this invention can be utilized to augment ex vivo therapeutic protocols as well. In the preferred practice of the invention, the vector is a recombinant adenoviral vector encoding the p53 tumor suppressor gene and MIP-3-α, wherein each gene is under the control of separate regulatory elements or both genes are under the control of a single regulatory element linked by an IRES element. In an alternative preferred embodiment, p53 and MIP-3-α are encoded on a selectively replicating adenoviral vector with MIP-3-α expressed off the Major Late Promoter. Further preferred embodiments of such adenoviral vectors employ selective deletions in the E1a region of the virus eliminating binding of E1a gene products from the p300 family members (p300 and CPB) and the pRb family members (Rb, p105 and p107). The vectors of the present invention also include recombinant viral vectors wherein the MIP-3-α gene is expressed in a vector comprising a pathway responsive promoter driving expression of an inhibitor of viral replication. The preferred vectors of the present invention may optionally include a cytokine gene such as IL4 and/or GM-CSF. In the most preferred practice of the invention, the vector comprises the a recombinant adenoviral vector in comprising a CMV-p53-IRES-MIP-3-α expression cassette.

The invention further provides pharmaceutical formulations comprising the vectors of the present invention. The compositions of the invention will be formulated for administration by manners known in the art acceptable for administration to a mammalian subject, preferably a human. In particular delivery systems may be formulated for intramuscular, intravenous, injectable depot type devices or topical administration.

The expression plasmid containing the therapeutic gene may be encapsulated in liposomes. Liposomes include emulsions, foams, micelles, insoluble monolayers, liquid crystals, phospholipid dispersions, lamellar layers and the like. The delivery of DNA sequences to target cells using liposome carriers is well known in the art. A variety of methods are available for preparing liposomes, as described in, e.g., Szoka et al. Ann. Rev. Biophys. Bioeng. 9:467 (1980), Szoka, et al. U.S. Pat. No. 4,394,448 issued Jul. 19, 1983, as well as U.S. Pat. Nos. 4,235,871, 4,501,728, 4,837,028, and 5,019,369, incorporated herein by reference. Liposomes useful in the practice of the present invention may be formed from one or more standard vesicle-forming lipids, which generally include neutral and negatively charged phospholipids and a sterol, such as cholesterol. Examples of such vesicle forming lipids include DC-chol, DOGS, DOTMA, DOPE, DOSPA, DMRIE, DOPC, DOTAP, DORIE, DMRIE-HP, n-spermidine cholesterol carbamate and other cationic lipids as disclosed in U.S. Pat. No. 5,650,096. The selection of lipids is generally guided by consideration of, e.g., liposome size, acid lability and stability of the liposomes in the blood stream. Additional components may be added to the liposome formulation to increase serum half-life such as polyethylene glycol coating (so called "PEG-ylation") as described in U.S. Pat. No. 5,013,556 issued May 7, 1991 and U.S. Pat. No. 5,213,804 issued May 25, 1993.

The compositions of the invention can also be administered in topical formulations or polymer matrices, hydrogel matrices, polymer implants, or encapsulated formulations to allow slow or sustained release of the compositions. When the delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of the compositions of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The compositions and methods of the present invention may be practiced alone or in combination with conventional chemotherapeutic agents or treatment regimens. Examples of such chemotherapeutic agents include inhibitors of purine synthesis (e.g., pentostatin, 6-mercaptopurine, 6thioguanine, methotrexate) or pyrimidine synthesis (e.g. Pala, azarbine), the conversion of ribonucleotides to deoxyribonucleotides (e.g. hydroxyurea), inhibitors of dTMP synthesis (5-fluorouracil), DNA damaging agents (e.g. radiation, bleomycines, etoposide, teniposide, dactinomycine, daunorubicin, doxorubicin, mitoxantrone, alkylating agents, mitomycin, cisplatin, procarbazine) as well as inhibitors of microtubule function (e.g. vinca alkaloids and colchicine). Chemotherapeutic treatment regimens refers primarily to non-chemical procedures designed to ablate neoplastic cells such as radiation therapy. Examples of combination therapy when the therapeutic gene is p53 are described in Nielsen, et al. WO/9835554A2 published Aug. 20, 1998. These chemotherapeutic agents may be administered seperately or may be included with the formulations of the present invention for co-administration.

I claim:

1. A recombinant adenoviral vector derived from human serotypes 2 or 5 which contains deletions in the E1a region so as to reduce binding of the E1a gene products to p300 and pRb protein family members wherein said vector expresses a dendritic cell chemoattractant.

2. The vector of claim 1 wherein said deletions comprise deletions of amino acids 4–25 and amino acids 111–123 of the E1a 243R and 289R proteins.

3. The vector of claim 2 wherein said adenoviral vector further comprises a p53 or TGF-β pathway responsive promoter which is upregulated in response to the presence of p53 or TGF-β, respectively, driving expression of an inhibitor of viral replication.

4. The vector of claim 3 wherein said inhibitor of viral replication is E2F-Rb.

5. The vector of claim 4 wherein the E1a gene is operably linked to an E2F pathway responsive promoter.

* * * * *